US010233472B2

(12) United States Patent
Ramsden et al.

(10) Patent No.: US 10,233,472 B2
(45) Date of Patent: *Mar. 19, 2019

(54) PREPARATION OF MALTO-OLIGOSACCHARIDES

(71) Applicant: Grain Processing Corporation, Muscatine, IA (US)

(72) Inventors: Steven L. Ramsden, Muscatine, IA (US); Zachary J. Halloran, Muscatine, IA (US); Albert J. Pollmeier, Muscatine, IA (US); Jeff M. Underwood, Muscatine, IA (US)

(73) Assignee: Grain Processing Corporation, Muscatine, IA (US)

( * ) Notice: Subject to any disclaimer, the term of this patent is extended or adjusted under 35 U.S.C. 154(b) by 152 days.

This patent is subject to a terminal disclaimer.

(21) Appl. No.: 15/461,980

(22) Filed: Mar. 17, 2017

(65) Prior Publication Data

US 2017/0183699 A1    Jun. 29, 2017

Related U.S. Application Data

(62) Division of application No. 14/826,354, filed on Aug. 14, 2015, now Pat. No. 9,637,767, which is a division
(Continued)

(51) Int. Cl.
| *C12P 19/14* | (2006.01) |
| *C12P 19/04* | (2006.01) |
| *C13K 7/00* | (2006.01) |
| *C08B 30/18* | (2006.01) |
| *C08B 30/04* | (2006.01) |

(52) U.S. Cl.
CPC ............ *C12P 19/14* (2013.01); *C08B 30/044* (2013.01); *C08B 30/18* (2013.01); *C12P 19/04* (2013.01);
(Continued)

(58) Field of Classification Search
None
See application file for complete search history.

(56) References Cited

U.S. PATENT DOCUMENTS 6,436,678 B2 * 8/2002 Antrim .................. C08B 30/18
127/38
9,163,269 B2 * 10/2015 Ramsden ................ C12P 19/14

FOREIGN PATENT DOCUMENTS

CN    101227834 A    7/2008
WO    WO-8908718 A1 *  9/1989    ............... A23L 2/78

OTHER PUBLICATIONS

Zhao et al, resistant starch prepared from high amylose maize starch with citric acid hydrolysis and its simulated fermentation in vitro, Eur Food Res Technol, 228:1015-1021 (Year: 2009).*

(Continued)

*Primary Examiner* — Melvin C. Mayes
*Assistant Examiner* — Stefanie J Cohen
(74) *Attorney, Agent, or Firm* — Fitch, Even, Tabin & Flannery LLP

(57) ABSTRACT

Disclosed is a method for preparing a mixture of malto-oligosaccharides. Generally, a dry-milled corn fraction, such as a corn flour from which germ and fiber have been removed, is subjected to hydrolysis, typically catalyzed with acid or an enzyme such as an α-amylase enzyme, under conditions suitable to form a mixture of malto-oligosaccharides. A gluten fraction is removed and the enzyme is inactivated, such as with heat. The mixture of malto-oligosaccharides then may be recovered from remaining solids and purified.

17 Claims, 5 Drawing Sheets

Related U.S. Application Data of application No. 14/200,972, filed on Mar. 7, 2014, now Pat. No. 9,163,269.

(60) Provisional application No. 61/787,067, filed on Mar. 15, 2013.

(52) U.S. Cl.
CPC ........ *C12Y 302/01001* (2013.01); *C13K 7/00* (2013.01)

(56) References Cited

OTHER PUBLICATIONS

Li et al, impact of alpha-amylase combined with HCl hydrolysis on structure and digestion of waxy rice starch, Jan. 2013, international journal of biological macromolecules 55, pp. 276-281 (Year: 2013).*

Yu et al, stagewise dilute acid pretreatmnet of enzyme hydrolysis of distillers grains and corn fiber, appli biochem biotechnol, 159: 553-567 (Year: 2009).*

Jiangsu, "New sugar source and its application," Province Sugar Food Science and Technology Information Station, Light Industry Press, published Aug. 31, 1991 (Machine translation).

Guanting Ling, "Manual for material of health food," Chemical Industry Press, published Feb. 28, 2002 (Machine translation).

Xiangbin Huang, et al., "Study on hydrolysis of wet-milling and dry-milling corn flour," Food Science and Technology vol. 6, published Dec. 31, 2001 (Abstract and machine translation).

Guozhi Zhao et al., "Starch saccharification process and its key technology," Grain set and oil vol. 10, published Oct. 31, 2007 (Abstract and machine translation).

Chinese Office Action for Application No. 201480011875.X dated Feb. 8, 2018 (Translation).

\* cited by examiner

PREPARATION OF MALTO-OLIGOSACCHARIDES

CROSS-REFERENCE TO RELATED APPLICATIONS

This application is a division of prior application Ser. No. 14/826,354, filed Aug. 14, 2015, now issued as U.S. Pat. No. 9,637,767 on Apr. 12, 2017, which is a division of prior application Ser. No. 14/200,972, filed Mar. 7, 2014, now issued as U.S. Pat. No. 9,163,269 on Oct. 20, 2015, which claims benefit of U.S. Provisional Application No. 61/787,067, filed Mar. 15, 2013. All prior applications are hereby incorporated herein by reference in their entireties.

TECHNICAL FIELD

The present disclosure relates to grain milling for purposes of recovering useful grain fractions.

BACKGROUND

Many oligosaccharides are commonly prepared by the control hydrolytic cleavage of starches. In the production of oligosaccharides, the glycosidic linkages of the starch molecules are partially hydrolyzed to yield at least one oligosaccharide species, and more typically, a mixture of oligosaccharide species. The oligosaccharide mixtures so prepared typically include at least one malto-oligosaccharide species. Malto-oligosaccharides are characterized as having a saccharide backbone that comprises predominantly 1-4 glycosidic linkages.

Malto-oligosaccharides may be characterized by their degree of polymerization (DP) which refers to the number of saccharide monomer units in each molecule. Each malto-oligosaccharide species also may be characterized by its dextrose equivalent value (DE) which is a measure of the reducing power of the malto-oligosaccharide relative to dextrose and which may be determined by the Lane and Eynon method or the Luff-Schoorl method as known in the art. Conventional malto-oligosaccharides generally are divided into maltodextrins and syrup solids. Malto-oligosaccharides having a DE of less than 20 are known as maltodextrins, whereas malto-oligosaccharides having a DE of 20 or greater are known as syrup solids.

Malto-oligosaccharides generally may be prepared via the corn wet milling process. In the corn wet mining process, corn is soaked in sulfur dioxide ($SO_2$) for a typical period of roughly 24-36 hours. This causes the corn kernel to separate into its four main component parts, which are germ, protein, fiber, and starch. The starch is then recovered and, when used for the production of malto-oligosaccharides, is subjected to enzymatically catalyzed hydrolysis to yield a mixture malto-oligosaccharides. The other component parts of the corn are used as feed or are themselves further processed to yield other commercially valuable products. The corn wet milling process is commercially practiced at present by Grain Processing Corporation of Muscatine, Iowa. Grain Processing Corporation is a commercial supplier of many food-grade malto-oligosaccharides sold under the MALTRIN® trademark. MALTRIN® malto-ologosaccharides are filtered, carbon-treated, and spray-dried products. The commercially available MALTRIN® product line covers a range of DE values from 5-25. Exemplary MALTRIN® products include MALTRIN® M040; MALTRIN® M100; MALTRIN® M150; MALTRIN® M180, and MALRTIN® QD grades M500, M510, M550, and M580.

The corn wet milling process, while well established, makes use of a substantial amount of sulfur dioxide. For some purposes it would be desirable to provide a method for production of malto-oligosaccharides that is capable of practice using less sulfur dioxide.

SUMMARY

It has now been found that malto-oligosaccharides can be prepared from dry-milled corn or other grain. Generally, a dry-milled corn fraction is provided. The corn fraction may be, for example, a corn fraction from which germ and fiber have been at least substantially removed. The corn fraction is then subjected to enzymatically catalyzed hydrolysis, preferably with an α-amylase enzyme, under conditions suitable to result in a mixture of malto-oligosaccharides. In further processing the enzyme then may be inactivated, such as with heat or by changing the pH, such as by adding acid. The mixture of malto-oligosaccharides having a DE of at most 70 then is recovered from remaining solids, such as by centrifugation. Surprisingly, a malto-oligosaccharide mixture comparable in purity to conventionally prepared malto-oligosaccharides may be prepared in some embodiments. Optionally, the mixture may be further purified, such as by filtration or treatment with activated carbon. Surprisingly, it has been found that the malto-oligosaccharides can have a protein content of less than 1% and an ash content of less than 2.5%. The method may be practiced in the substantial absence of sulfur dioxide and other sulfurous additives.

The method may but need not include the steps of dry milling corn to form a corn product and preparing a fraction from the corn product, such as by separating germ and fiber to result in a corn fraction from which at substantially all of said germ and fiber had been removed.

In other embodiments, not mutually exclusive with respect to the above, the invention encompasses a product prepared by providing a corn fraction, such as a fraction from which germ and fiber have been at least substantially removed, the corn fraction having been prepared from a dry-milled corn product; subjecting said corn fraction to enzymatically catalyzed hydrolysis under conditions suitable to result in a mixture of malto-oligosaccharides, and terminating the hydrolysis to form a mixture of malto-oligosaccharides having a DE of at most 70. This product is itself valuable as an intermediate in the preparation of more purified malto-ologosaccharides.

The method may be practiced using sulfur dioxide in certain steps, but in many embodiments may be practiced using less sulfur dioxide per unit weight of corn than the conventional wet milling process.

DETAILED DESCRIPTION OF THE PREFERRED EMBODIMENT

Figure 1:
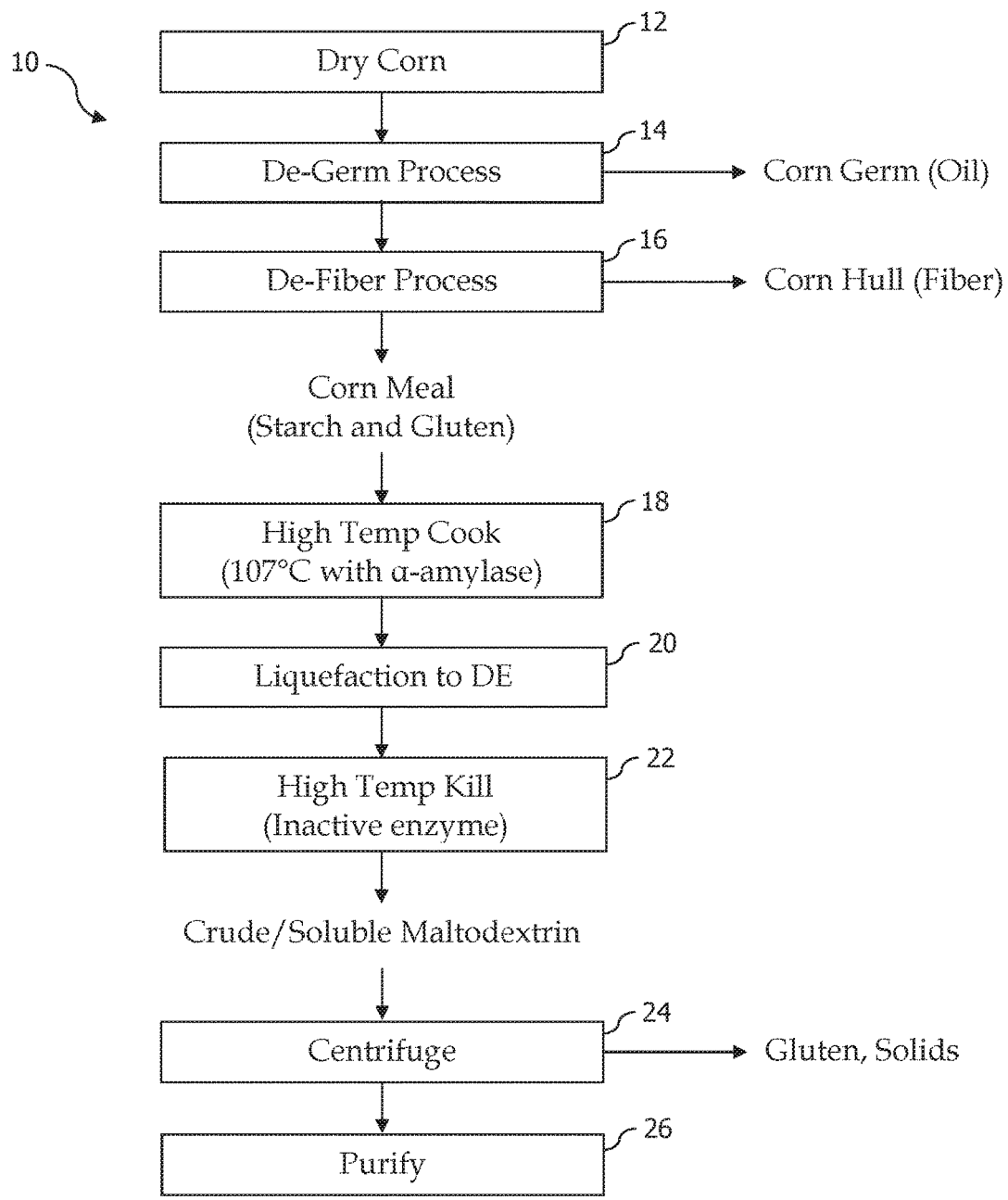
FIG. 1 is a flow chart that generally represents steps in one embodiment of the process described herein.

The remainder of the description herein will be specified with respect to corn, but it should be understood that the subject matter described herein is equally applicable to other starch-bearing grains, such as wheat, rice, potato, and tapioca. Any suitable corn may be used in connection with the invention, for instance, yellow dent corn.

Generally, the disclosed embodiments pertain to the production of malto-oligosaccharides, or mixtures of predominantly 1-4 linked glucosyl units. In many embodiments, at least 50% of the saccharide units in the malto-oligosaccharide prepared in accordance with the present teachings are linked via 1-4 linkages; in many embodiments, at least 55%; in many embodiments at least 60%; in many embodiments at least 65%; in many embodiments at least 70%; in many embodiments at least 75%; in many embodiments at least 80%; in many embodiments at least 85%; in many embodiments at least 90%; and in many embodiments at least 95% of the saccharide units in the malto-oligosaccharide are linked via 1-4 linkages. Malto-oligosaccharides are contemplated to include saccharides species that have an odd DP value and in many cases the mixture of malto-oligosaccharides will include some dextrose (DP 1). The malto-oligosaccharides may have a DE of any conventional value, and thus, for instance, the DE of the mixture of malto-oligosaccharides may be 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70. In some embodiments the DE of the mixture of malto-oligosaccharides may range from 3-25 and in some embodiments from 5-25. In some embodiments the mixture is a maltodextrin and in other embodiments the mixture is a syrup or syrup solid. In other embodiments the DE is less than 50. For instance, the mixture of malto-oligosaccharides may have a DE of less than 49, less than 48, less than 47, less than 46, less than 45, less than 44, less than 43, less than 42, less than 41, less than 40, less than 39, less than 38, less than 37, less than 36, less than 35, less than 34, less than 33, less than 32, less than 31, less than 30, less than 29, less than 28, less than 27, less than 26, less than 25, less than 24, less than 23, less than 22, less than 21, less than 20, less than 19, less than 18, less than 17, less than 16, less than 15, less than 14, less than 13, less than 12, less than 11, less than 10, less than 9, less than 8, less than 7, less than 6, less than 5, less than 4, or less than 3.

Further details concerning maltodextrins and applications for maltodextrins can be found in U.S. Pat. No. 7,728,125 "Reduced malto-oligosaccharides"; U.S. Pat. No. 7,595,393 "Reduced malto-oligosaccharides"; U.S. Pat. No. 7,405,293 "Reduced malto-oligosaccharides"; U.S. Pat. No. 7,265,078 "Drilling fluid apparatus and method"; U.S. Pat. No. 7,091,335 "Derivatized reduced malto-oligosaccharides"; U.S. Pat. No. 6,946,148 "Method for absorbing fluid"; U.S. Pat. No. 6,919,446 "Reduced malto-oligosaccharides"; U.S. Pat. No. 6,828,310 "Compositions including reduced malto-oligosaccharide preserving agents, and methods for preserving a material"; U.S. Pat. No. 6,806,231 "Drilling fluid, apparatus, and method"; U.S. Pat. No. 6,720,418 "Derivatized reduced malto-oligosaccharides"; U.S. Pat. No. 6,613,898 "Reduced malto-oligosaccharides"; U.S. Pat. No. 6,610,672 "Compositions including reduced malto-oligosaccharide preserving agents, and methods for preserving a material"; U.S. Pat. No. 6,593,469 "Compositions including reduced malto-oligosaccharide preserving agents"; U.S. Pat. No. 6,528,629 "Malto-oligosaccharide derived glycosides"; U.S. Pat. No. 6,518,223 "Drilling fluid, apparatus, and method"; U.S. Pat. No. 6,475,979 "Reduced malto-oligosaccharide cleansing compositions"; U.S. Pat. No. 6,436,678 "High purity maltose process and products"; U.S. Pat. No. 6,391,293 "Lanthionizing compositions, systems, and methods"; U.S. Pat. No. 6,380,379 "Derivatized reduced malt-oligosaccharides"; and U.S. Pat. No. 6,375,798 "Derivatized malto-oligosaccharides, methods for trash scavenging, and process for preparing a paper web"; all assigned to Grain Processing Corporation of Muscatine, Iowa.

Generally, the invention contemplates preparation of a malto-oligosaccharide mixture from a dry-milled corn fraction. "Dry" does not connote the complete absence of moisture, and to the contrary it is understood that the corn will contain some moisture as is naturally present and/or as is introduced to remove from the corn during conventional shipping, handling, and storage. It is contemplated in some embodiments that dry-milled corn itself is subjected to enzymatically catalyzed hydrolysis. In many embodiments, however, it is a fraction of the corn that is subjected to enzymatically catalyze hydrolysis. For example, the corn fraction may be a dry-milled corn fraction from which corn germ has been removed. In other embodiments, the dry-milled corn fraction can be a fraction from which fiber has been removed. In many cases, the dry-milled corn fraction can be a fraction from which both germ and fiber had been removed. By "removed" in this context is contemplated the least substantial removal of the indicated components via conventional or otherwise suitable techniques. For example, the removal of fiber is described in Singh et al., "Recovery of Fiber in the Corn Dry-grind Ethanol Process: A Feed Stock for Valuable Coproducts," *Cereal Chem.* 76 (6:868-72) (1999) and removal of germ is described in Singh et al., "Effect of Corn Oil on Stillage Evaporators," *Cereal Chem.* 76 (6:846-49) (1999).

For comparison to known processes, with reference now to FIG. 1, one generalized process 10 is shown. At step 12, dry corn is provided. The corn is de-germed and fiber is removed, as shown in steps 14 and 16 respectively, to form a flour from which germ and fiber are removed. The invention is not limited to practice using such a flour, and it is contemplated that other corn fractions may be employed. In the illustrated embodiment, the resulting flour contains both starch and corn gluten. To this fraction in step 18 is added an enzyme, generally an α-amylase enzyme, and the temperature is brought to any temperature suitable for allowing the enzyme to be operative to catalyze the hydrolysis of the starches in the corn fraction. In some embodiments, the temperature is 100-200° F.; in the illustrated embodiment, the temperature is 107° F. Any suitable enzyme may be employed and it is contemplated that the temperature may be brought to an optimal operating temperature for the enzyme. The enzyme may be added in any amount relative to the solids weight; for example, 0.02-0.4% of the solids weight.

Figure 2:
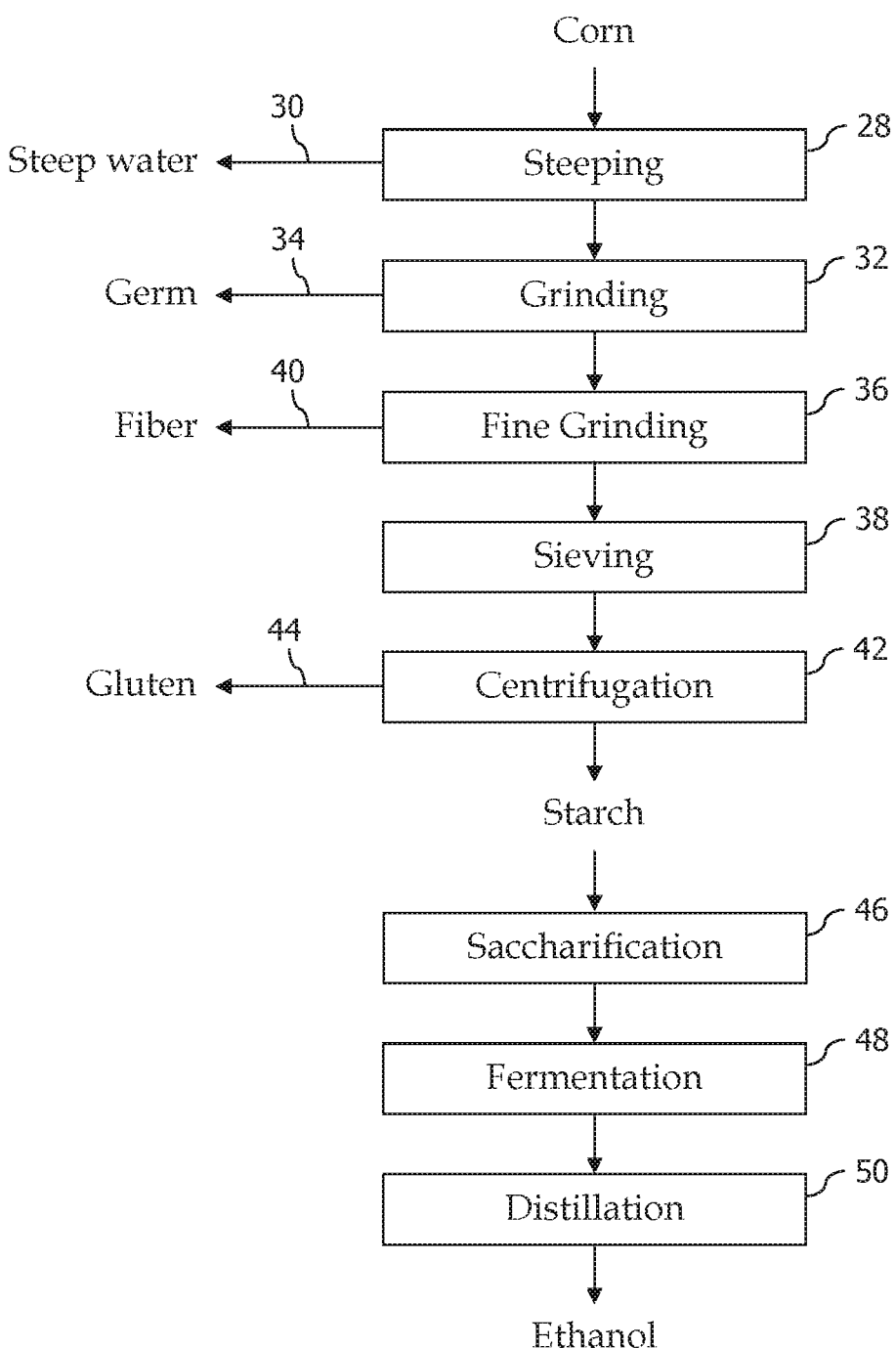
FIG. 2 is a flow chart that generally representing steps in a conventional wet milling process used for ethanol production.

In accordance with the exemplary process shown in FIG. 2, as shown in step 20, liquefaction is allowed to proceed until the desired DE is attained. Those of skilled in the art will recognize that the exact amount of time of necessity will vary depending on factors such as temperature and enzyme, but it is believed that a period of time ranging from 5 to 50 hours; in some embodiments 24-36 hours, may be sufficient in many cases to yield a mixture of malto-oligosaccharides within a desired range of DE values. At step 22, the enzyme is inactivated, generally by elevating the temperatures sufficient to neutralize the enzyme.

The resulting fraction is a crude fraction that comprises malto-oligosaccharides in an aqueous mixture. Via subsequent steps, as shown in step 24, the malto-oligosaccharides may be separated from gluten and other remaining solids in the mixture. As shown at step 26, the malto-oligosaccharides may be subjected to purification steps such as filtration and carbon treatment. Subsequently or prior thereto, the mixture may be dried, such as by drum or spray drying.

The protein content of the corn fraction is typically greater than 5%, some of which is soluble protein in the wet milling process. Surprisingly, it has been found that the malto-oligosaccharides prepared in accordance with the teachings described herein can have a protein content of less than 1%. Some of the protein originally present in the corn is ordinarily soluble when the corn is processed using the wet milling process to form malto-oligosaccharides, and it was unexpectedly found that the protein content of the malto-oligosaccharides produced upon centrifugation, where the soluble malto-oligosaccharides are separated from other components, contained a lower-than-expected amount of protein.

In some embodiments, the protein content is less than 0.9%; in some embodiments, less than 0.8%; in some embodiments, less than 0.7%; in some embodiments, less than 0.6%; in some embodiments, less than 0.5% by dry solids weight. Similarly, the malto-oligosaccharides prepared in accordance with the teachings described herein can have an ash content of less than 2.5%; in some embodiments, less than 2.4%; in some embodiments, less than 2.3%; in some embodiments, less than 2.2%; in some embodiments, less than 2.1%; in some embodiments, less than 2.0%; in some embodiments, less than 1.9%; in some embodiments, less than 1.8%; in some embodiments, less than 1.7%; in some embodiments, less than 1.6%; in some embodiments, less than 1.5%; in some embodiments, less than 1.4%; in some embodiments, less than 1.3%; in some embodiments, less than 1.2%; in some embodiments, less than 1.1%; in some embodiments, less than 1.0%; in some embodiments, less than 0.9%; in some embodiments, less than 0.8%; in some embodiments, less than 0.7%; in some embodiments, less than 0.6%; in some embodiments, less than 0.5% by dry solids weight.

The above process has been demonstrated with respect to enzymatically catalyzed hydrolysis, but it should be understood that the invention is not limited thereto. Any suitable process for hydrolyzing starch to yield malto-oligosaccharides can be employed. In some embodiments, the hydrolysis is catalyzed with mineral or other acids, such as citric or other food grade acids, and in some embodiments, the hydrolysis is catalyzed with an acid and one or more enzymes. In some cases an acid and an enzyme can be employed sequentially in either order as may be appropriate.

By comparison to the conventional wet milling process shown in FIG. 2, corn is provided, and is steeped at step 28 using sulfur dioxide to cause the corn to separate into its four major components. As shown at 30, the steep water is removed, and the corn proceeds to grinding at step 32 and de-germination at step 34. Fine grinding and sieving occur at steps 36 and 38 respectively, with fiber removal at step 40. The resulting product is centrifuged at step 42 and gluten is removed at 44, thus yielding starch. The starch is then saccharified at step 46, typically to dextrose. The dextrose is then fermented and distilled to form ethanol, as shown in steps 48 and 50 respectively.

Figure 5:
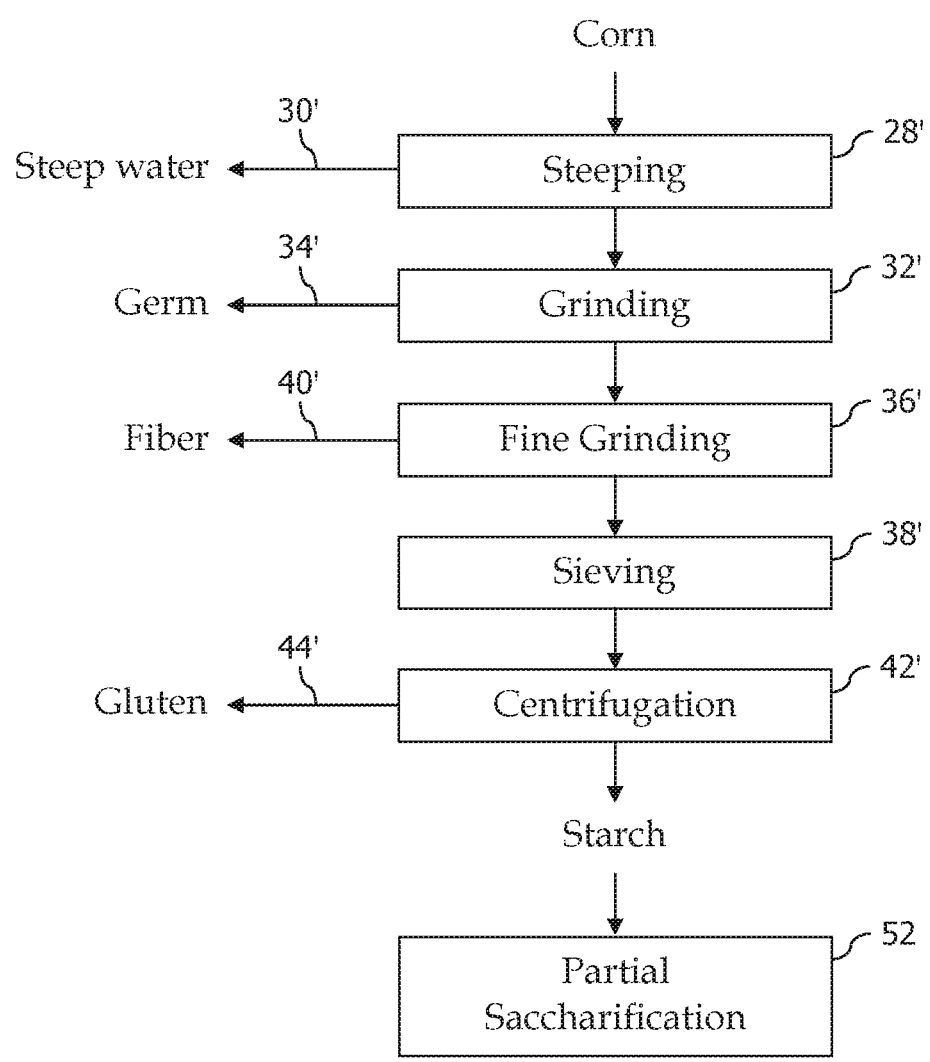
FIG. 5 is a flow chart generally representing steps in a process for preparing maltodextrin from starch in a conventional corn wet milling process

Alternatively, as shown in FIG. 5, the starch may be liquefied via partial saccharification at step 52 using enzymatically catalyzed hydrolysis to form malto-oligosaccharides. In FIG. 5, corn is provided, and is steeped at step 28' using sulfur dioxide to cause the corn to separate into its four major components. As shown at 30', the steep water is removed, and the corn proceeds to grinding at step 32' and de-germination at step 34'. Fine grinding and sieving occur at steps 36' and 38' respectively, with fiber removal at step 40'. The resulting product is centrifuged at step 42' and gluten is removed at 44', thus yielding starch. FIGS. 2 and 5 are idealized flow charts and in practice various modifications will be apparent to those of skill in the art.

Figure 3:
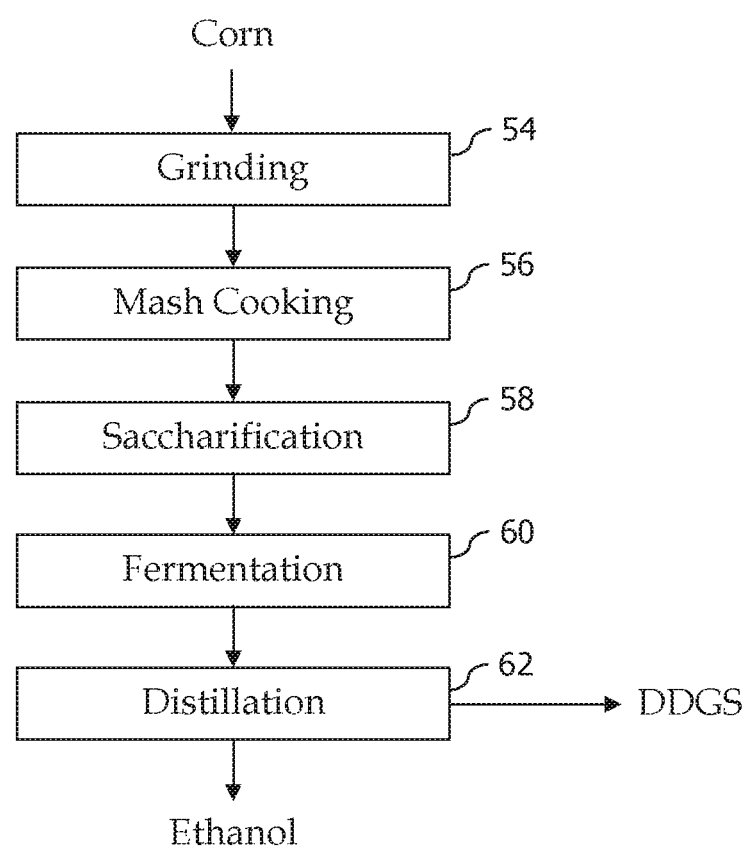
FIG. 3 is a flow chart representing generally steps in a dry milling process for ethanol production.

With respect to the ethanol production process from dry milling as shown in FIG. 3, corn is ground, as shown in step 54, and is then mash cooked at step 56. The resulting mixture is saccharified at step 58, and the product is fermented at step 60 and distilled at step 62, typically to a eutectic mixture of ethanol and water. Besides ethanol, the resulting product is known as distillers dried grains with solubles ("DDGS").

Figure 4:
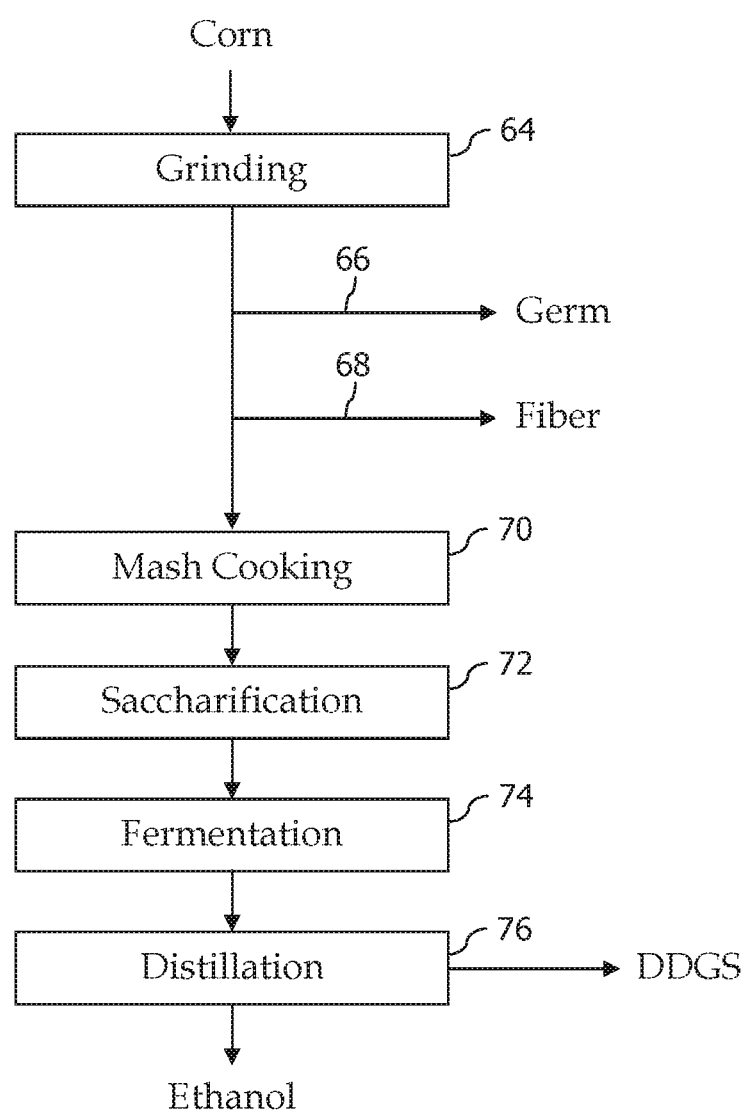
FIG. 4 is a flow chart representing generally steps in a "quick germ" dry grind process.

Singh, V. and others (see Singh et al. "Comparison of Modified Dry-grind Corn Processes for Fermentation Characteristics and DDGS Composition," *Cereal Chem.* 82 (2): 187-490 (2005) and Singh et al., "Recovery of Fiber in the Corn Dry-grind Ethanol Process: A Feedstock for Valuable Coproducts," *Cereal Chem.* 82 (76):868-72 (1999)) have proposed processed term "quick germ" and "quick germ quick fiber." Briefly, and as described in Wahjudi et al., "Quick Fiber Process: Effect of Mash Temperature, Dry Solids, and Residual Germ on Fiber Yield and Purity," *Cereal Chem.* 77 (5):640-44 (2000), as shown in FIG. 4, corn is ground at step 64, and at steps 66 and 68, germ and fiber are removed respectively. The remaining product is mash cooked at step 70, and saccharified at step 72. The resulting product is then treated much as in the conventional starch process, with the starch being fermented to dextrose at step 74 and the ethanol thus form distilled at step 76 to yield eutectic ethanol and DDGS.

The following Examples are provided to illustrate certain embodiments of the disclosed invention but should not be construed as limiting the scope of the invention.

EXAMPLES

Example 1

De-germinated corn flour having the following chemical analysis was provided:

| | |
|---|---|
| Fat (%, dsb) | 0.8 |
| Ash (%, dsb) | 0.4 |
| Protein (%, dsb) | 5.2 |
| Moisture (%) | 8.7 |
| Starch (%, dsb) | 82.5 |

The corn flour was slurried in water at 25% solids. Then, Valley Research Ultra Thin 100L enzyme (as-is solution) was added to the corn flour slurry at a rate 0.1% wt. based on solids weight. The slurry was then cooked using a steam jet cooker with temperature setting at around 220° F. for 1.0 minutes. The cooked starch was held in containers for 90 to 120 minutes at 195 to 200° F. to allow the enzyme to hydrolyze the starch. Samples were taken to measure DE of the starch hydrolysates. When a targeted DE was achieved, solution of citric acid (50% w/w) solution was added to the slurry to bring its pH to 4.0 to 4.2. Then the starch hydrolysate slurry was cooked in a jet cooker at 210° F. to 220° F. to inactivate the enzyme. The enzyme inactivated hydrolysate was then centrifuged on a Sharpies P660 decanter centrifuge to remove insoluble solids. Activated carbon like SA-1500 from MeadWestvaco Corporation, in an amount of 1.5% weight of starch hydrolysate solid weight, was then mixed into the centrifuged hydrolysate slurry. The slurry was held at 185° F. for 30 min with mixing. Then the slurry was filtered using a rotary filter with Celatom Diatomaceous Earth FW 40 pre-coat filter aid to remove insoluble materials. The filtrate was then collected and spray-dried.

The slurry was analyzed before centrifugation and found to have the following analysis:

| Slurry before centrifuge | |
|---|---|
| Test | Result |
| Moisture (%) | 84.3 |
| Solids (%) | 15.7 |
| DE | 16.9 |
| Protein (%, dsb) | 8.7 |

The centrifuge liquid was found to have the following chemical analysis:

| Liquid from Centrifuge | |
|---|---|
| Test | Result |
| Moisture (%) | 83.8 |
| Solids (%) | 16.2 |
| DE | 14.9 |
| Protein (%, dsb) | 1.4 |

Example 2

The de-germinated corn flour used in Example 1 was slurried in water at 25% solids. Then, DSM Veritase enzyme (as-is solution) was added to the corn flour slurry at a rate 0.1% wt. based on solids weight. The slurry was then cooked using a steam jet cooker with temperature setting at around 220° F. for 10 minutes. The cooked starch was held in containers for 90 to 120 minutes at 195 to 200° F. to allow the enzyme to hydrolyze the starch. Samples were taken to measure DE of the starch hydrolysates. When a targeted DE was achieved, solution of citric acid (50% w/w) solution was added to the slurry to bring its pH to 4.0 to 4.2. Then the starch hydrolysate slurry was cooked in a jet cooker at 210° F. to 220° F. to inactivate the enzyme. The enzyme inactivated hydrolysate was then centrifuged on a Flottweg Z23-3/441 decanter centrifuge to remove insoluble solids. Activated carbon like SA-1500 from MeadWestvaco Corporation, in an amount of 1.5% weight of starch hydrolysate solid weight, was then mixed into the centrifuged hydrolysate slurry. The slurry was held at 185° F. for 30 min with mixing. Then the slurry was filtered using a rotary filter with Celatom Diatomaceous Earth FW 40 pre-coat filter aid to remove remaining insoluble matters. The filtrate was then collected and spray-dried.

The slurry was analyzed and found to have the following chemical analysis:

| Slurry before centrifuge | |
|---|---|
| Test | Result |
| Moisture (%) | 81.0 |
| Solids (%) | 19.0 |
| DE | 12.2 |
| Protein (%, dsb) | 1.6 |

In addition, the liquid from the centrifuge and the finished product after drying were analyzed and found to have the following analyses.

| Test | Result |
|---|---|
| Liquid from Centrifuge | |
| Moisture (%) | 82.2 |
| Solids (%) | 17.8 |
| DE | 22.1 |
| Protein (%, dsb) | 0.4 |
| Finished product | |
| Moisture (%) | 3.4 |
| Ash (%, dsb) | 0.7 |
| Protein (%, dsb) | 0.3 |
| DE | 23.3 |

The maltodextrin prepared in accordance with this Example was surprisingly pure, with protein and ash content each below 1%. It is believed that the increase in DE as between the centrifuge liquid and the dried product may be due to retention of large malto-oligosaccharide species on the filter during the purification step.

Example 3

The de-germinated corn flour used in Example 1 was slurried in water at 25% solids. Then, DSM Veritase enzyme (as-is solution) was added to the corn flour slurry at a rate 0.1% based on solids weight. The slurry was then cooked using a steam jet cooker with temperature setting at around 220° F. for 8 minutes. The cooked starch was then heated to around 280° F. for 2 minutes to deactivate the enzyme. Then, the slurry was cooled to around 210° F. and Validase BAA 1500L enzyme was added to the cooked slurry at a rate of 0.1% wt based on solids weight. The cooked starch was held in containers for 180 to 240 minutes at 195 to 200° F. to allow the enzyme to hydrolyze the starch. Samples were taken to measure DE of the starch hydrolysates. When a targeted DE was achieved, solution of citric acid (50% w/w) solution was added to the slurry to bring its pH to 4.0 to 4.2. Then the starch hydrolysate slurry was cooked in a jet cooker at 210° F. to 220° F. to inactivate the enzyme. The enzyme inactivated hydrolysate was then centrifuged on a Flottweg Z23-3/441 decanter centrifuge to remove insoluble solids. The centrifuged slurry was then filtered in a Graver Technologies microfilter with a pore size of 0.1 micron. The filtered hydrolysate was then treated by passing through a bed of PAD900 adsorbent resin from Purolite. The treated solution was then collected and spray-dried. The products produced had a DE range from 3 to 25. The slurry before centrifugation and the centrifuge mud and liquid were evaluated and found to have the following chemical analyses:

| Slurry Before Centrifuge | |
|---|---|
| Moisture (%) | 78.7 |
| Solids (%) | 21.3 |
| DE | 13 |
| Protein (%, dsb) | 4.1 |
| Centrifuge Mud | |
| Moisture (%) | 67.8 |
| Fat (%, dsb) | 1.1 |
| Ash (%, dsb) | 0.9 |
| Protein (%, dsb) | 14.4 |
| Starch (%, dsb) | 57.4 |
| Liquid from Centrifuge | |
| Moisture (%) | 78.1 |
| DE | 11.4 |
| Protein (%, dsb) | 2.5 |

A product having a DE of 14.4 was evaluated and found to have the following chemical analysis:

| Finished Product | |
|---|---|
| Moisture (%) | 3.8 |
| Ash (%) dsb | 0.4 |
| Protein (%) as is | 0.3 |
| DE | 14.4 |

The maltodextrin prepared in accordance with this Example was surprisingly pure, with protein and ash content each below 0.5%.

Example 4

The de-germinated corn flour used in Example 1 was slurried in water at 25% solids. Then, HCl was added to the corn flour slurry to adjust the conductivity to 1200 to 1600 μS/cm. The slurry was then cooked using a steam jet cooker with temperature setting at around 265° F. for 10 minutes. Then, the slurry was cooled to around 210° F. and a slurry of soda ash (diluted to 5 baume) was added to the hydrolysate to adjust the pH to 6.4 to 6.8 and Validase BAA 1500L enzyme was added to the cooked slurry at a rate of 0.02% wt. based on solids weight. The cooked starch was held in containers for 180 to 240 minutes at 195 to 200° F. to allow the enzyme to hydrolyze the starch. Samples were taken to measure DE of the starch hydrolysates. When a targeted DE was achieved, solution of HCl was added to the slurry to bring its pH to 4.0 to 4.2. Then the starch hydrolysate slurry was cooked in a jet cooker at 210° F. to 220° F. to inactivate the enzyme. The enzyme inactivated hydrolysate was then centrifuged on a Flottweg Z23-3/441 decanter centrifuge to remove insoluble solids. The centrifuged slurry was then filtered in a Graver Technologies microfilter with a pore size of 0.1 micron. The filtered hydrolysate was then treated by passing through a bed of PAD900 adsorbent resin from Purolite. The treated solution was then collected and spray-dried.

The slurry before centrifugation, centrifuge mud, and liquid from the centrifuge were analyzed and found to have the following chemical analyses:

| Test | Result |
|---|---|
| Slurry before centrifuge | |
| Moisture (%) | 84.7 |
| Solids (%) | 15.3 |
| DE | 17.2 |
| Protein (%, dsb) | 5.9 |
| Centrifuge Mud | |
| Moisture (%) | 66.1 |
| Fat (%, dsb) | 0 |
| Ash (%, dsb) | 0.6 |
| Protein (%, dsb) | 13.8 |
| Starch (%, dsb) | 63.1 |
| Liquid from Centrifuge | |
| Moisture (%) | 84.8 |
| Solids (%) | 15.2 |
| DE | 19.4 |
| Protein (%, dsb) | 3.9 |

Example 5

A de-germinated corn flour having the following chemical analysis was provided:

| Fat (%, dsb) | 1.4 |
|---|---|
| Ash (%, dsb) | 0.7 |
| Protein (%, dsb) | 5.8 |
| Moisture (%) | 12.3 |
| Starch (%, dsb) | 83.6 |

The de-germinated corn flour was slurried in water at 25% solids. Then, HCl was added to the corn flour slurry to adjust the conductivity to 1200 to 1600 μS/cm. The slurry was then cooked using a steam jet cooker with temperature setting at around 265° F. for 10 minutes. Then, the slurry was cooled to around 210° F. and a slurry of soda ash (diluted to 5 baume) was added to the hydrolysate to adjust the pH to 6.4 to 6.8 and Validase BAA 1500 L enzyme was added to the cooked slurry at a rate of 0.02% wt. based on solids weight. The cooked starch was held in containers for 180 to 240 minutes at 195 to 200° F. to allow the enzyme to hydrolyze the starch. Samples were taken to measure DE of the starch hydrolysates. When a targeted DE was achieved, solution of HCl was added to the slurry to bring its pH to 4.0 to 4.2. Then the starch hydrolysate slurry was cooked in a jet cooker at 210° F. to 220° F. to inactivate the enzyme. The enzyme inactivated hydrolysate was then centrifuged on a Flottweg Z23-3/441 decanter centrifuge to remove insoluble solids. Activated carbon like SA-1500 from MeadWestvaco Corporation, 1.5% weight of starch hydrolysate solid weight, was then mixed into the centrifuged hydrolysate slurry. The slurry was held at 185° F. for 30 min with mixing. Then the slurry was filtered using a rotary filter with Celatom Diatomaceous Earth FW 40 pre-coat filter aid to remove remaining insoluble matters. The filtrate was then collected and spray-dried.

The slurry before centrifugation and the centrifuge mud and liquid were evaluated and found to have the following chemical analyses:

| Slurry Before Centrifuge | |
|---|---|
| Moisture (%) | 83.1 |
| Solids (%) | 16.9 |

-continued

| | |
|---|---|
| DE - Osmometer | 14.7 |
| Protein (%, dsb) | 5.3 |
| Centrifuge Mud | |
| Moisture (%) | 70.8 |
| Fat (%, dsb) | 0.2 |
| Ash (%, dsb) | 0.7 |
| Protein (%, dsb) | 12.5 |
| Starch (%, dsb) | 62.3 |
| Liquid from Centrifuge | |
| Moisture (%) | 81.8 |
| Solids (%) | 18.2 |
| DE - Osmometer | 15.1 |
| Protein (%, dsb) | 2.0 |

The spray-dried maltodextrin was evaluated and found to have the following chemical analysis:

| | |
|---|---|
| Moisture (%) | 4.1 |
| Ash (%) dsb | 2.1 |
| Protein (%) as is | 0.4 |
| DE (Schoorl) | 13.9 |

The maltodextrin prepared in accordance with this Example was surprisingly pure, with protein content below 0.5%.

It is thus seen that a method for preparation of malto-oligosaccharides and malto-oligosaccharide product are provided.

Except as otherwise clearly indicated by context, all weight percentages expressed herein are on a dry solids basis.

All references cited herein are hereby incorporated by reference in their entireties.

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A method of preparing a mixture of malto-oligosaccharides, said method comprising:
    providing a dry-milled corn fraction from which fiber has been at least substantially removed;
    subjecting said corn fraction to hydrolysis under aqueous conditions suitable to produce an aqueous hydrolysate, said hydrolysate comprising a mixture of malto-oligosaccharides;
    treating the hydrolysate to remove insoluble solids and to recover an aqueous fraction containing at least a portion of said mixture of malto-oligosaccharides; and
    recovering said mixture of malto-oligosaccharides from said aqueous fraction, the recovered mixture of malto-oligosaccharides having a protein content of less than 1% by dry solids weight.

2. A method according to claim 1, said corn fraction being subjected to hydrolysis with an acid.

3. A method according to claim 2, said acid comprising citric acid.

4. A method according to claim 1, said corn fraction being subjected to hydrolysis with an acid and hydrolysis with an enzyme.

5. A method according to claim 4, said hydrolysis with the acid and said hydrolysis with the enzyme being carried out sequentially in either order.

6. A method according to claim 4, said enzyme comprising an α-amylase enzyme.

7. A method according to claim 1, said dry-milled corn fraction also having had germ at least substantially removed therefrom.

8. A method according to claim 1, said treating the hydrolysate to remove insoluble solids comprising centrifuging the hydrolysate.

9. A method according to claim 1, further comprising purifying said aqueous fraction.

10. A method according to claim 9, said purifying comprising passing said aqueous fraction through a filter.

11. A method according to claim 9, said purifying comprising treatment with activated carbon.

12. A method according to claim 9, said purifying comprising passing said aqueous fraction through an adsorbent resin.

13. A method according to claim 9, said purifying comprising at least two of passing said aqueous fraction through a filter, treatment with activated carbon, and passing said aqueous fraction through an adsorbent resin.

14. A method according to claim 1, said recovering comprising spray-drying said aqueous fraction.

15. A method according to claim 1, said recovering comprising drum-drying said aqueous fraction.

16. A method according to claim 1, said recovered mixture of malto-oligosaccharides having a DE of less than 50.

17. A method according to claim 16, said recovered mixture of malto-oligosaccharides having a DE of 3 to 25.

* * * * *